US012733804B2

(12) United States Patent
Baker et al.

(10) Patent No.: US 12,733,804 B2
(45) Date of Patent: Sep. 15, 2026

(54) TECHNIQUES FOR QUANTITATIVELY ASSESSING TEAR-FILM DYNAMICS

(71) Applicant: Alcon Inc., Fribourg (CH)

(72) Inventors: Kevin Baker, Duluth, GA (US); Hyo Won Choi, Keller, TX (US); David Borja, Suwanee, GA (US); Carolina Kunnen, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 965 days.

(21) Appl. No.: 17/855,445

(22) Filed: Jun. 30, 2022

(65) Prior Publication Data

US 2023/0049316 A1 Feb. 16, 2023

Related U.S. Application Data

(60) Provisional application No. 63/232,081, filed on Aug. 11, 2021.

(51) Int. Cl.
*A61B 3/10* (2006.01)
*A61B 3/107* (2006.01)
(Continued)

(52) U.S. Cl.
CPC .............. *A61B 3/101* (2013.01); *A61B 3/107* (2013.01); *A61B 3/145* (2013.01); *G02C 7/027* (2013.01);
(Continued)

(58) Field of Classification Search
CPC ......... A61B 3/101; A61B 3/107; A61B 3/145; G02C 7/027; G06T 7/11;
(Continued)

(56) References Cited

U.S. PATENT DOCUMENTS 8,888,286 B2 * 11/2014 Grenon ................ A61B 3/1005 351/221
2008/0309872 A1 12/2008 Hara et al.
(Continued)

FOREIGN PATENT DOCUMENTS

JP 2006204773 A 8/2006
JP 2020093076 A 6/2020

OTHER PUBLICATIONS

Doane Marshall, EP 0232986 A1; Method And Apparatus For In Vivo Ocular Wetting Determinations (Year: 1987).*
(Continued)

*Primary Examiner* — Wyatt A Stoffa
*Assistant Examiner* — Irahman Abduri
(74) *Attorney, Agent, or Firm* — Nicholas Smith

(57) ABSTRACT

Aspects of the present disclosure provide techniques for quantitatively assessing tear-film dynamics associated with contact lenses. An example method includes projecting an image of one or more shapes on a tear film surface of the contact lens worn on the eye, capturing video data, comprising a plurality of image frames, of the one or more shapes projected on the tear film surface of the contact lens over a period of time, performing image segmentation on a plurality of reflection patterns included in the plurality of image frames, generating a plurality of maps of the tear film surface of the contact lens indicating changes to the tear film surface of the contact lens during the period of time, and outputting, based on the plurality of maps, one or more metrics quantifying the changes to the tear film surface of the contact lens over the period of time.

20 Claims, 7 Drawing Sheets

(51) Int. Cl.
*A61B 3/14* (2006.01)
*G02C 7/02* (2006.01)
*G06T 7/11* (2017.01)

(52) U.S. Cl.
CPC ...... *G06T 7/11* (2017.01); *G06T 2207/10016* (2013.01); *G06T 2207/20081* (2013.01); *G06T 2207/30041* (2013.01)

(58) Field of Classification Search
CPC . G06T 2207/10016; G06T 2207/20081; G06T 2207/30041
USPC .......................................................... 351/205
See application file for complete search history.

(56) References Cited

U.S. PATENT DOCUMENTS

2014/0104574 A1* 4/2014 Grenon ................ A61B 3/0025 351/246
2015/0031993 A1* 1/2015 Buckland ............... A61B 3/102 600/425
2021/0158525 A1 5/2021 Iwase et al.

OTHER PUBLICATIONS

Amni Batrisyia Shamsul Amri Nur, et al., An Overview of Dry Eye Analysis Algorithms for Tear Film Break-Up time Detection, 2021 IEEE Symposium on Industrial Electronics and Applications, Jul. 10, 2021, 1-6, N/A, ISIEA, IEEE.
Craig Jennifer P., et al., The TFOS International workshop on Contact Lens Discomfort: Report of the Contact Lens Interactions With the Tear Film Subcommittee, Investigative Opthalmology and Visual Science, Oct. 18, 2013, TFOS123, 54:11.
Kopf Miriam, et al., Tear Film Surface Quality with Soft Contact Lenses Using Dynamic Videokeratoscopy, Journal of Optometry, Jan. 1, 2008, 14-21, 1:1.
Mousavi Maryam, et al., The utility of measuring team file break-up time for prescribing contact lenses, Contact Lens and Anterior Eye, Aug. 30, 2017, 105-109, 41, No. 1, Stockton Press, Basingstoke, GB.

* cited by examiner

TECHNIQUES FOR QUANTITATIVELY ASSESSING TEAR-FILM DYNAMICS

BACKGROUND

In the human eye, the precorneal tear film covering ocular surfaces is composed of three primary layers: the mucin layer, the aqueous layer, and the lipid layer. Each layer plays a role in the protection and lubrication of the eye and thus affects dryness of the eye or lack thereof. Dryness of the eye is a recognized ocular disease, which is generally referred to as "dry eye," "dry eye syndrome" (DES), or "keratoconjunctivitis sicca" (KCS). Dry eye can cause symptoms, such as itchiness, burning, and irritation, which can result in discomfort. There is a correlation between the ocular tear film layer thicknesses and dry eye disease.

For wearers of contact lenses, a widely reported ailment to physicians is intolerance to prolonged contact lens usage. Contact lens wear can contribute to dry eye. A contact lens can disrupt the natural tear film and can reduce corneal sensitivity over time, which can cause a reduction in tear production. In some patients, contact lens wear becomes unmanageable due to pain, irritation, or general decrease of visual acuity due to ocular discomfort. Typical remedies include repetitive eye drop applications, alterations of daily activity, or repeated removal of the contact lenses and return to standard eyeglasses or poor vision. For physicians, a typical treatment regime of revised medications and replacement contact lenses is tried and evaluated until a recommendation to alternative vision correction is employed for the patient. For many of these patients, evaporative dry eye disease is an underlying cause for their contact lens intolerance.

SUMMARY

In certain embodiments, a method for tear film analysis of a contact lens worn on an eye is provided. The method includes projecting an image of one or more shapes on a tear film surface of the contact lens worn on the eye. The method further includes capturing video data of the one or more shapes projected on the tear film surface of the contact lens over a period of time, wherein the video data comprises a plurality of image frames and each image frame of the plurality of image frames includes a reflection pattern of the one or more shapes at a particular point in time at which that image frame is captured. The method further includes performing image segmentation on the reflection pattern of each of the plurality of image frames. The method further includes generating a plurality of maps of the tear film surface of the contact lens based on the image segmentation performed on the plurality of the reflection patterns, the plurality of maps indicating changes to the tear film surface of the contact lens during the period of time. The method further includes outputting, based on the plurality of maps, one or more metrics quantifying the changes to the tear film surface of the contact lens over the period of time In certain embodiments, an imaging apparatus is provided for tear film analysis of a contact lens worn on an eye. The imaging apparatus includes a corneal topographer configured to project an image of one or more shapes on a tear film surface of the contact lens worn on the eye. The imaging apparatus also includes a digital camera configured to capture video data of the one or more shapes projected on the tear film surface of the contact lens over a period of time, wherein the video data comprises a plurality of image frames and each image frame of the plurality of image frames includes a reflection pattern of the one or more shapes at a particular point in time at which that image frame is captured. The imaging apparatus also includes at least one processor, coupled with a memory, configured to cause the imaging apparatus to perform image segmentation on the reflection pattern of each of the plurality of image frames. Additionally, the at least one processor may be configured to cause the imaging apparatus to generate a plurality of maps of the tear film surface of the contact lens based on the image segmentation performed on the plurality of the reflection patterns, the plurality of maps indicating changes to the tear film surface of the contact lens during the period of time. Additionally, the at least one processor may be configured to cause the imaging apparatus to output, based on the plurality of maps, one or more metrics quantifying the changes to the tear film surface of the contact lens over the period of time.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments described herein provide optical systems, devices, and techniques for obtaining ophthalmic information associated with contact lens wear. The ophthalmic information may be used to quantitatively assess tear-film dynamics of a patient's eye associated with the contact lens wear. In some embodiments, the ophthalmic information may include video data used to generate a plurality of maps indicating changes to tear-film surface of the contact lens. In some embodiments, based on the plurality of maps one or more metrics may be output that quantify the changes to the tear-film surface.

Figure 1B:
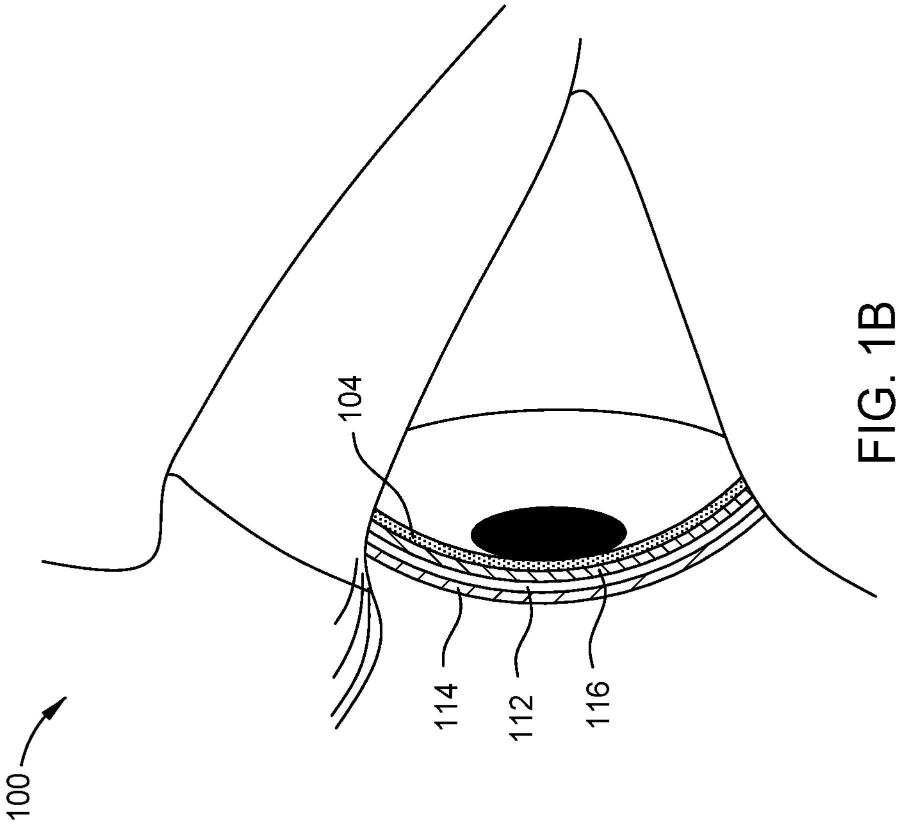
FIGS. 1A and 1B illustrate various tear films of a patient's eye with and without a contact lens.
Figure 1A:
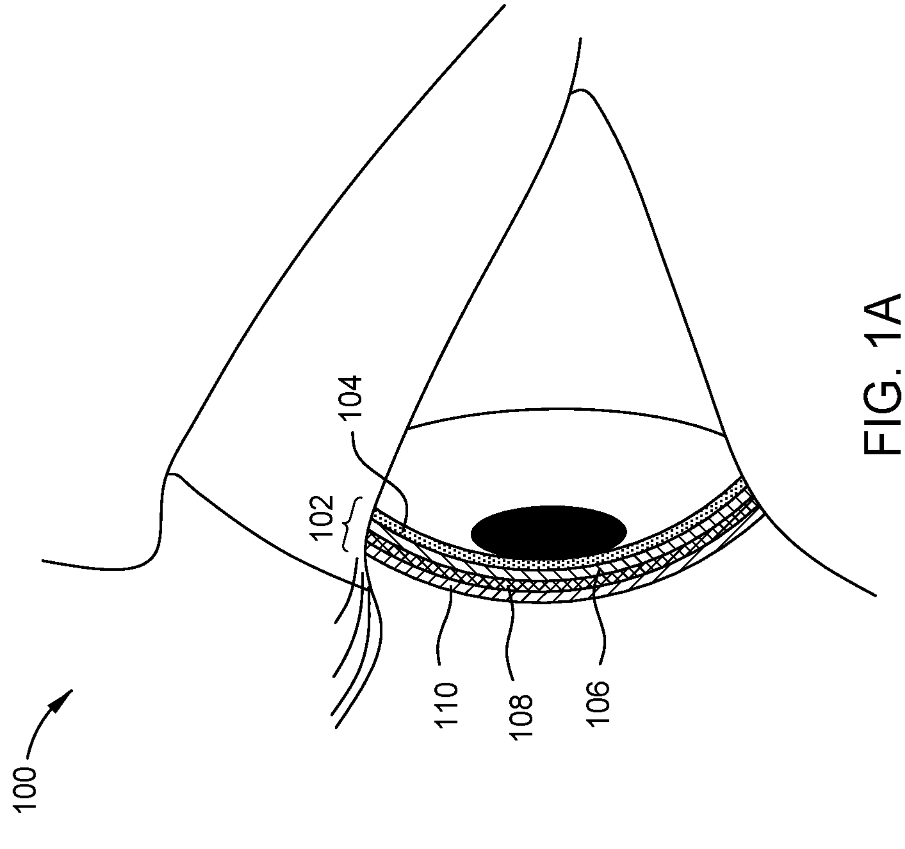

FIGS. 1A and 1B illustrate various tear films of a patient's eye 100 with and without a contact lens. As illustrated in FIG. 1A, the eye 100 includes a precorneal tear film 102 comprising a plurality of different sublayers. For example, an innermost layer of the tear film 102 is shown in contact with cornea 104 of the eye 100, known as the mucus layer 106. The mucus layer 106 may be comprised of mucins, providing lubrication and a protective layer to assist in the retention of moisture on the cornea 104 and prevent dryness of the eye 100.

The tear film 102 also includes a middle or aqueous layer 108 comprising the bulk of the tear film 102. The aqueous layer 108 is formed by secretion of aqueous by lacrimal glands and accessory tear glands surrounding the eye 100. The aqueous secreted by the lacrimal glands and accessory tear glands is also commonly referred to as "tears." One function of the aqueous layer 108 is to help flush out any dust, debris, or foreign objects that may get into the eye 100. Another important function of the aqueous layer 108 is to provide lubrication and a protective layer to keep the eye 100 moist and comfortable. Defects that cause a lack of sufficient aqueous in the aqueous layer 14, also known as "aqueous deficiency," are a common cause of dry eye.

As shown, the tear film 102 also includes a lipid layer 110, which aids in preventing dryness of the eye. The lipid layer 110 is comprised of lipids known as "meibum" or "sebum" that is produced by meibomian glands in upper and lower eyelids of the eye 100. This lipid layer 110 is very thin, typically less than 250 nanometers (nm) in thickness. The lipid layer 110 provides a protective coating over the aqueous layer 108 to limit the rate at which the aqueous layer 108 evaporates. Blinking causes the upper eyelid to mall up aqueous and lipids as a tear film, thus forming a protective coating over the eye 100. A higher rate of evaporation of the aqueous layer 108 can cause dryness of the eye. Thus, if the lipid layer 110 is not sufficient to limit the rate of evaporation of the aqueous layer 108, dryness of the eye may result.

In many cases, a patient may choose to wear a contact lens in order to correct for poor vision, which may affect the functionality of the tear film of the eye 100 as illustrated in FIG. 1B. For example, when a contact lens 112 is applied to the eye 100, additional fluid from either the packaging solution or the care regimen of the contact lens 112 initially dilutes the tears/aqueous of the eye 100. Once in position on the cornea 104, the contact lens 112 splits the tear film 102 into two distinct layers known as the pre-lens tear film 114 and the post-lens tear film 116. As shown, the pre-lens tear film 114 covers an outer surface of the contact lens 112 while the post-lens tear film 116 is disposed between the contact lens 112 and the cornea 104.

In a healthy eye, tear film thickness is about 7 micrometers (μm); however, once the contact lens 112 (which has a typical center thickness of at least 70 μm) has been applied to and has settled on the cornea 104 of the eye 100, the pre-lens tear film 114 is only about 1 μm to 2 μm. As such, the pre-lens tear film 114 covering the outer surface of the contact lens 112 has a thinner lipid layer, an increased evaporation rate, and a reduced tear volume compared with the normal tear film 102 illustrated in FIG. 1A. These changes may destabilize the tear film and may result in patients reporting dry eye symptoms during contact lens wear.

Dry eye in a patient may be diagnosed using techniques that measure a break-up time of the tear film of the patient's eye. Generally, a tear film break-up time value of approximately 10 to 35 seconds is considered as normal (i.e., the patient may be considered not to have dry eye). Conversely, when a patient has a tear film break-up time value less than 10 seconds, the tear film of the patient may be considered unstable and, as such, the patient may be experiencing eye dryness and discomfort. Contact lenses may have a direct impact on tear film break-up times. For example, in some cases, when soft contact lenses are worn, the tear break-up time typically reduces from 15 to 30 seconds prior to insertion to fewer than 10 seconds, irrespective of the material or wear regimen of the contact lens.

One manner of measuring the tear film break-up time involves the use of a corneal topographer to project a known pattern onto a surface of the tear film on the cornea of a patient's eye and a camera to record the reflection of the known pattern off of the patient's cornea. The recorded reflection may be used to detect any distortions in the known pattern, which may signify a break-up of the tear film on the cornea of the patient's eye.

Figure 2:
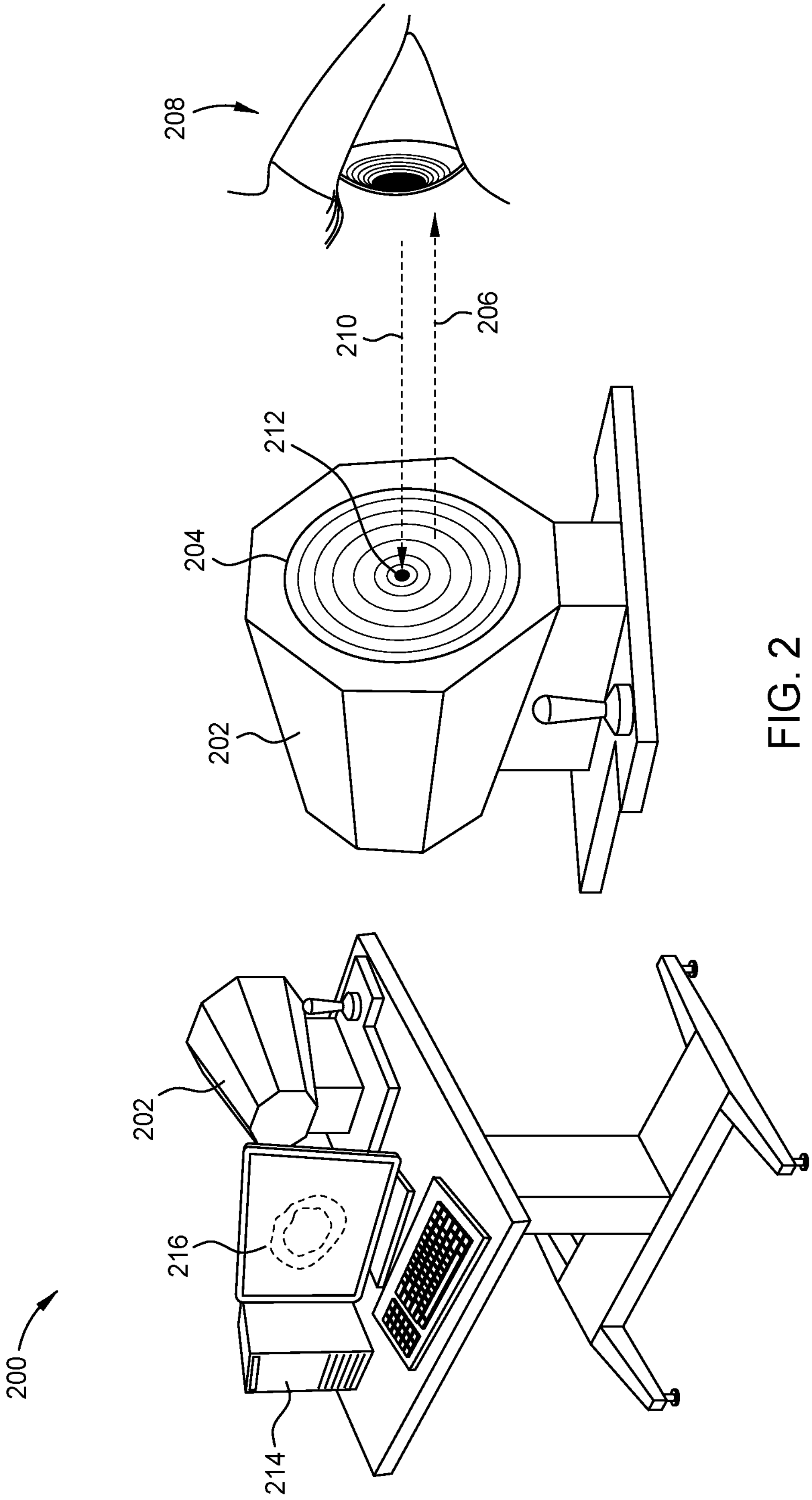
FIG. 2 illustrates an example environment including a corneal topographer for measuring a break-up time of the tear film of a patient's eye, according to certain embodiments.

FIG. 2 illustrates an example environment 200 including a corneal topographer for measuring a break-up time of the tear film of a patient's eye. For example, as illustrated, the environment 200 includes a corneal topographer 202. The corneal topographer 202 includes a placido disk 204 comprising a pattern of concentric rings. The placido disk 204 may be backlit by a light source, allowing for the pattern of concentric rings to be projected, as shown with arrow 206, onto a surface of a tear film of a patient's eye 208 positioned in front of the placido disk 204. The projected pattern of concentric rings may then be reflected off of the tear film of the patient's eye 208, as shown with arrow 210.

As shown, the corneal topographer 202 also includes a camera 212, such as a digital camera, which may be used to record video of the reflection of the pattern of concentric rings projected onto the tear film surface of the patient's eye. The video recorded by the camera 212 of the corneal topographer 202 may then be input into/stored in a computer 214 and displayed on a monitor 216. To determine a break-up time of tear film, a physician may instruct the patient to blink while the camera 212 is recording the reflection of the pattern of concentric rings projected onto the tear film surface of the patient's eye. After the patient blinks, the physician and/or hardware/software in the computer 214 may monitor the video captured by the camera 212 for any distortions in the pattern of concentric rings reflected from the tear film surface of the patient's eye. Any distortion to the pattern of concentric rings reflected from the tear film surface of the patient's eye may indicate that the tear film surface has broken up and the patient's eye has begun to dry. The time interval between the patient's last blink and detection of a distortion in the pattern of concentric rings reflected from the tear film surface of the patient's eye gives a singular tear film breakup time metric associated with the patient's eye.

However, while the techniques presented above may be used to determine a break-up time of a tear film of a patient's eye, the techniques described above for assessing tear film dynamics, such as the techniques described above for determining the singular tear film breakup time, provide limited value and are often variable (e.g., results are not reproducible), inadequate, and not intended for use when wearing a contact lens. Moreover, the tear film metrics described above (e.g., the singular tear film breakup time) inadequately describe tear film dynamics and frequently do not correlate well with clinical outcomes, such as comfort associated with wearing contact lenses, visual performance of contact lenses, and the like. Yet further, quantitative tear film comparisons (e.g., comparisons of tear film breakup times) between different contact lens designs and lubricating eye drop solutions is difficult under different testing conditions and patient populations using the techniques described above.

Accordingly, aspects of the present disclosure provide techniques for quantitatively assessing tear-film dynamics of patient's eye associated with contact lens use. In some cases, quantitatively assessing tear-film dynamics may be based on ophthalmic information associated with the patient's eye and the contact lens wear. The ophthalmic information may include, for example, video data of a tear film surface of a contact lens worn on the patient's eye, which may be used to generate a plurality of maps indicating changes to the tear film surface. Further, based on the plurality of maps, one or more metrics may be output that quantify the changes to the tear-film surface.

In some cases, the one or more metrics determined/output according to the techniques described herein provide more information than the singular tear film breakup time described above, which only provides a time at which a breakup occurs but fails to provide any sort of additional information associated with the breakup such as velocity, acceleration, magnitude, location, and the like. As such, the one or more metrics determined according to the techniques described herein include, for example, at least one of a tear film breakup velocity, a tear film breakup acceleration, a tear film break magnitude, or a tear film breakup location (e.g., peripheral portion of a contact lens, a central portion of the contact lens, etc.). These additional metrics may quantify tear film dynamics more accurately, allowing for clinical outcomes, such as comfort associated with wearing contact lenses and visual performance of contact lenses, to be assessed more accurately.

Additionally, the techniques and the one or more metrics described may be used to provide other useful information/recommendations associated with contact lenses, which may not otherwise be possible with the singular tear film breakup time metric described above. For example, in some cases, the recommendations generated based on the techniques and one or more metrics described herein may include at least one of a recommendation to manufacture the contact lens with certain manufacturing materials, a recommendation to use certain eye drops with the contact lens, a recommendation to change a shape of the contact lens, or a recommendation to use the contact lens with eyes with a particular corneal shape.

Figure 3:
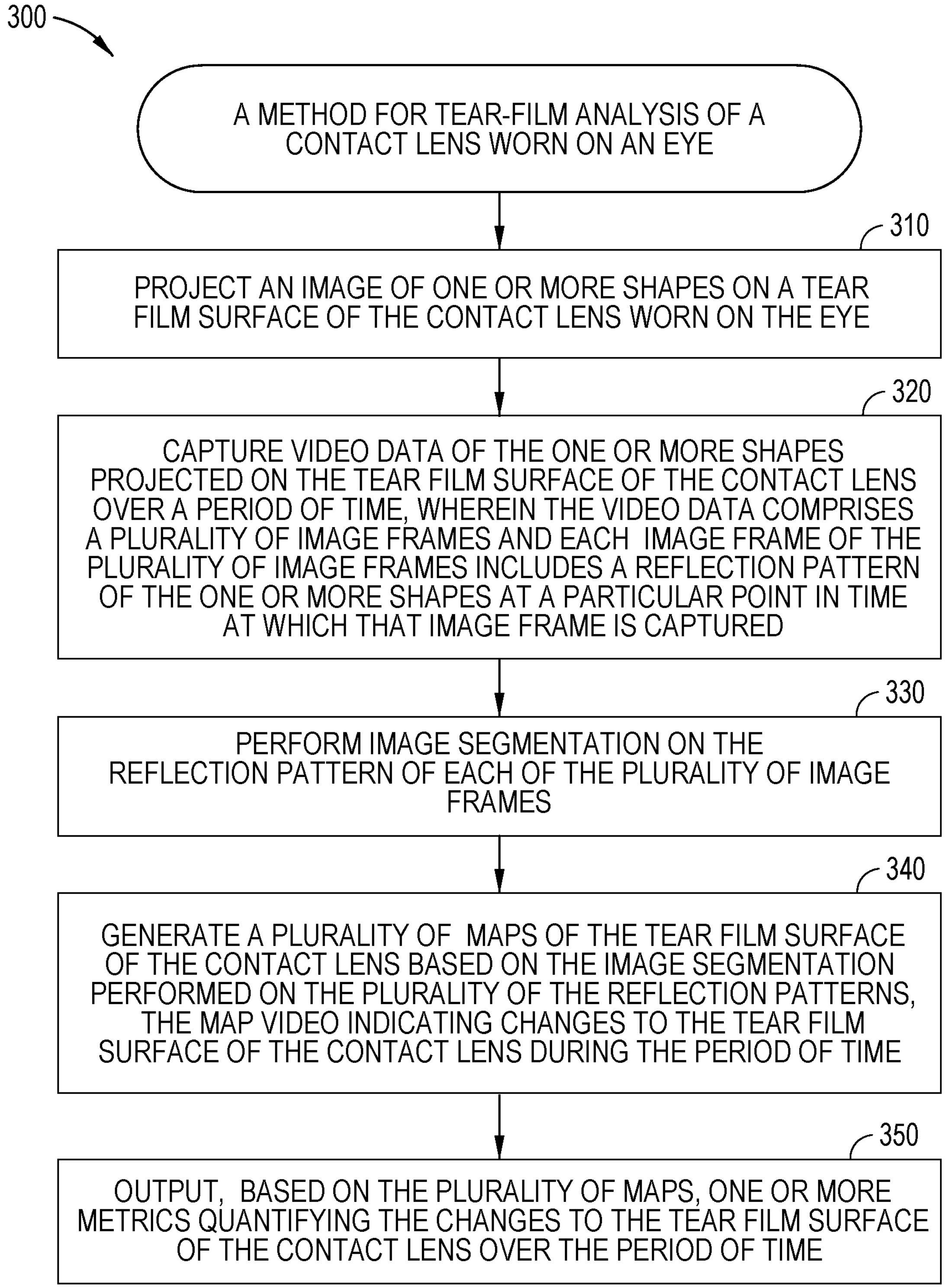
FIG. 3 illustrates an example process for tear film analysis of a contact lens worn on an eye, according to certain embodiments.

FIG. 3 illustrates an example process 300 for tear film analysis of a contact lens worn on an eye. In some embodiments, the process 900 may be performed by an imaging apparatus, such as the computer 214 in combination with the corneal topographer 202 and camera 212.

The process 300 begins at block 310 with the imaging apparatus (e.g., via the corneal topographer 202) projecting an image of one or more shapes on a tear film surface of the contact lens worn on the eye. In some cases, the one or more shapes may include one or more placido rings. For example, as described above with respect to FIG. 2, the corneal topographer 202 may be used to project an image of the placido disk 204 on to a tear film surface of a contact lens worn on the eye 208. While the techniques presented herein are described in relation to projecting an image of one or more placido rings, it should be understood that any type of known pattern (e.g., a matrix of dots or other one or more shapes) may be used and projected on the eye rather than placido rings.

Thereafter, at block 320, the imaging apparatus (e.g., via the camera 212) captures video data of the one or more placido rings projected on the tear film surface of the contact lens over a period of time. The video data may include a plurality of image frames and each image frame of the plurality of image frames includes a reflection pattern of the one or more placido rings (e.g., as shown at 210 in FIG. 2) at a particular point in time at which that image frame is captured. In some cases, the period of time over which the video data (including the plurality of image frames) is captured may include a period of time between ocular blinks of the eye.

Figure 4A:
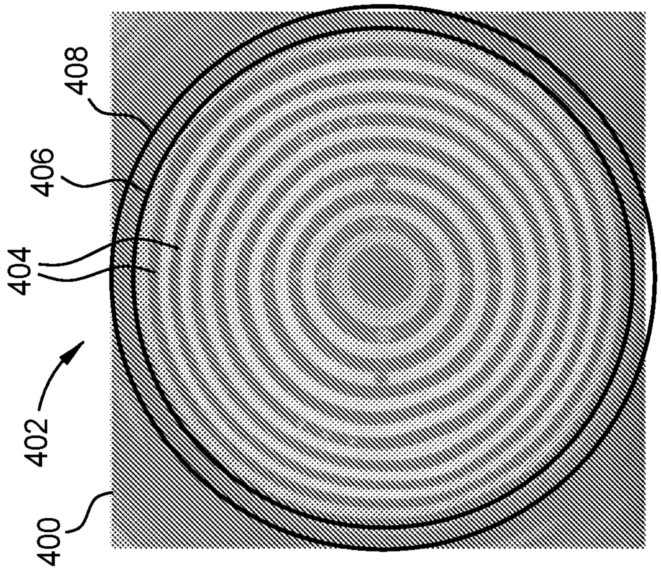
FIG. 4A illustrates an example of a first image frame of video data captured by an imaging apparatus, according to certain embodiments.

FIG. 4A illustrates an example of a first image frame 400 of the video data captured by the imaging apparatus. As shown, the first image frame 400 includes a reflection pattern 402 of placido rings 404 projected on to the tear film surface of a contact lens 406 of a patient's eye 408. In some embodiments, the first image frame 400 may be captured shortly after the patient blinks and may serve as a basis for determining changes to the tear film surface of the contact lens 406 worn on the patient's eye 408, as described below. Generally, right after the patient blinks, the tear film surface of the contact lens 406 will be intact and no changes may be observed.

Returning to FIG. 3, at block 330, the imaging apparatus performs image segmentation on a reflection pattern of each of the plurality of image frames. In some embodiments, the imaging apparatus may perform the image segmentation to determine edges of the one or more placido rings in each reflection pattern. In some cases, performing image segmentation to determine the edges of the one or more placido rings may include analyzing the reflection pattern in an image frame to identify points in the reflection pattern of the image frame with discontinuities or sharp changes in brightness. In some cases, such analysis may involve analyzing brightness or intensity, color, or the like between pixels of the image frame.

Figure 4B:
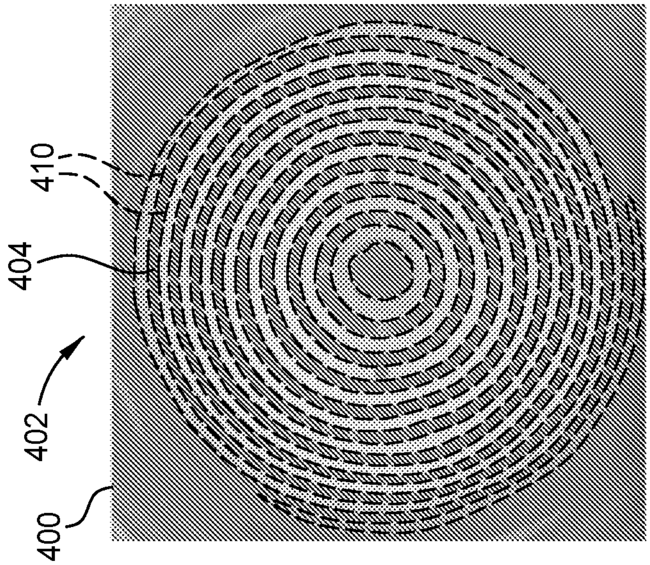
FIG. 4B illustrates an example of image segmentation performed on a reflection pattern in the first image frame of video data captured by the imaging apparatus, according to certain embodiments.

FIG. 4B illustrates an example of this image segmentation. For example, as illustrated, the imaging apparatus may perform image segmentation on the reflection pattern 402 in the first image frame 400 to determine edges 410 of the placido rings 404. In some embodiments, the imaging apparatus may perform the image segmentation based on an artificial intelligence (AI) model trained to perform image segmentation of images including reflection patterns associated with contact lenses. More specifically, for example, the AI model may be trained specifically for determining edges of one or more placido rings in reflection patterns reflected off of tear film surfaces of contact lenses.

After performing image segmentation on the first image frame 400 of the video data, the imaging apparatus may perform image segmentation on additional image frames of the video data. For example, FIG. 5A illustrates a second image frame 500 of the video data, which includes a reflection pattern 502 of the placido rings 404 projected on to the tear film surface of a contact lens 406 of a patient's eye 408. In some embodiments, the second image frame 500 may be taken at a second point in time after the first image frame 400 and may be used (directly or indirectly), in combination with the first image frame 400, to determine changes to the tear film surface of the contact lens 406, as described below.

Figure 5B:
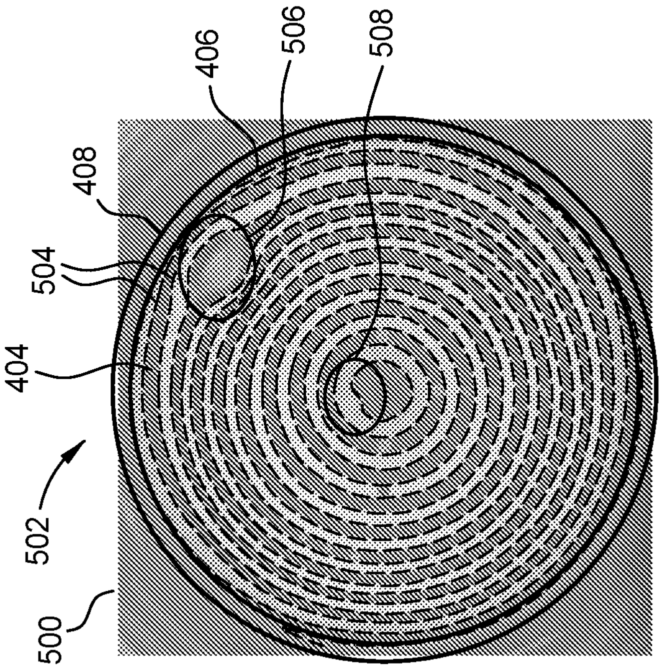
FIG. 5B illustrates an example of image segmentation performed on reflection pattern in the second image frame of video data captured by the imaging apparatus, according to certain embodiments.
Figure 5A:
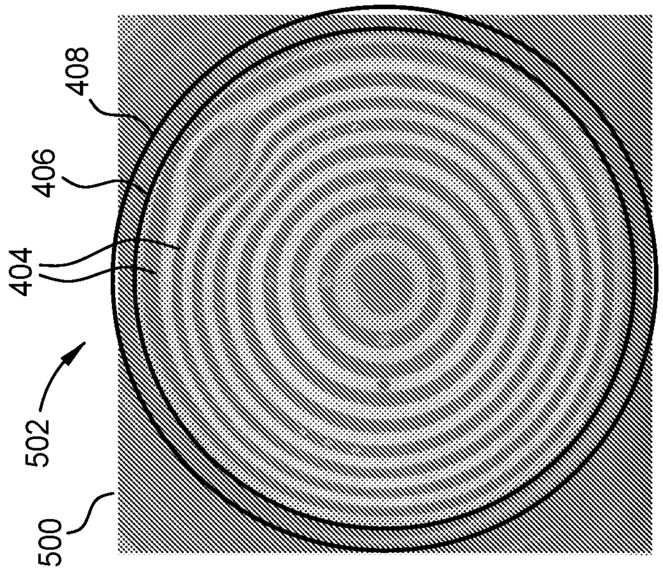
FIG. 5A illustrates an example of a second image frame of video data captured by the imaging apparatus, according to certain embodiments.

Thereafter, as shown in FIG. 5B, The imaging apparatus may then perform image segmentation on the second image frame 500 to determine edges 504 of the placido rings 404 in the reflection pattern 502. As noted above, the second image frame 500 is captured at a second point of time after the first image frame 400 is captured by the imaging apparatus. During the time interval between when the first image frame 400 is captured and the second image frame 500 is captured, the tear film on the contact lens 406 may begin to evaporate and deteriorate, eventually resulting in a change to the tear film, such as a breakup of the tear film. For example, as illustrated in the second image frame 500, a first change 506 of the tear film of the contact lens 406 is shown in a peripheral portion of the contact lens 406 and a second change 508 of the tear film of the contact lens 406 is shown in a center portion of the contact lens 406. In some cases, the first change 506 and second change 508 may be breakups of the tear film of the contact lens 406 or may be areas in which the tear film of the contact lens 406 has evaporated sufficiently (even though the tear film is still intact) to cause a displacement of an edge of the placido rings 404. The imaging apparatus may quantify these changes to the tear film using a plurality of displacement maps generated based on the image segmentation performed on the reflection patterns of the image frame of the video data, as described below.

While aspects of the present disclosure only illustrate two different image frames, namely the first image frame 400 of FIG. 4A and second image frame 500 of FIG. 5A, it should be understood that the imaging apparatus may capture (and subsequently perform image segmentation on and generate displacement maps based on) any number of image frames during the period of time over which the video data is captured (e.g., between ocular blinks).

For example, at block 340 of FIG. 3, the imaging apparatus generates a plurality of displacement maps of the tear-film surface of the contact lens based on the image segmentation performed on the plurality of the reflection patterns. In some embodiments, the plurality of maps may form a map video and may indicate changes to the tear-film surface of the contact lens during the period of time over which the video data at block 320 is captured. To generate the plurality of displacement maps, the imaging apparatus may track the locations (e.g., in polar coordinates, Cartesian coordinates, etc.) of the edges of the one or more placido rings (e.g., determined based on the image segmentation performed at block 330 of FIG. 3) across the plurality of image frames in the video data. For example, the imaging apparatus may compare the locations of the edges of the one or more placido rings across the plurality of image frames and, based on the comparisons of the edge locations, may generate the plurality of displacement maps indicating changes to the locations of the edges of the one or more placido rings during the period of time over which the video data is captured. In some cases, the plurality of maps may show a magnitude of displacement of the edges of the one or more placido rings from one image frame to the next during the period of time over which the video data is captured.

As noted above, rather than projecting an image of the one or more placido rings on the tear film surface of the contact lens 406, any known pattern may be used, such as a matrix of dots. For example, in such cases, the imaging apparatus may project a matrix of dots on to the tear film surface of the contact lens 406. The imaging apparatus may then capture the video data including the plurality of image frames (including the exemplary first image frame 400 and the second image frame 500) during a period of time (e.g., between ocular blinks). Each image frame of the plurality of image frames in this case may include a reflection pattern of the matrix of dots at a particular point in time at which that image frame is captured. The imaging apparatus may then perform image segmentation on the reflection patterns in each of the plurality of image frames to determine edges (and locations) of dots of the matrix of dots projected onto the tear film surface of the contact lens 406. The imaging apparatus may then track the edges/locations of dots across the plurality of image frames. For example, the imaging apparatus may compare the locations of the edges of the dots across the plurality of image frames and, based on the comparisons of the edge locations, may generate the plurality of displacement maps indicating changes to the locations of the edges of the dots during the period of time over which the video data is captured.

Figure 6A:
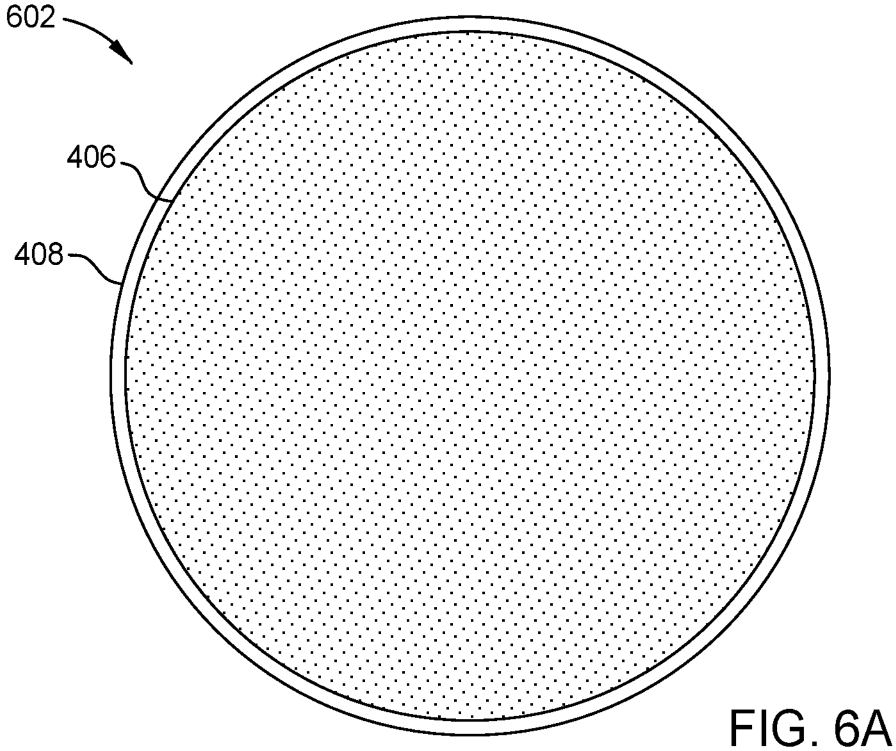
FIGS. 6A and 6B illustrate example displacement maps generated based on the image segmentation performed on the reflection patterns in the first and second image frames, according to certain embodiments.
Figure 6B:
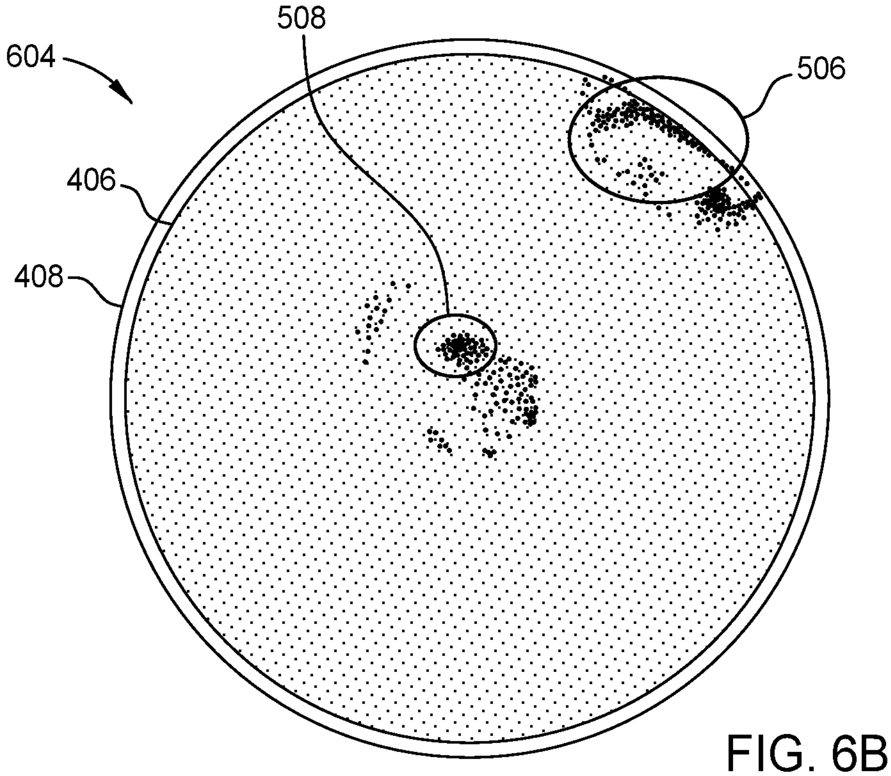

FIGS. 6A and 6B illustrate example displacement maps generated based on the image segmentation performed at block 330 on the plurality of the reflection patterns. For example, FIG. 6A illustrates a first displacement map 602 corresponding to the reflection pattern 402 of the placido rings 404 in the first image frame 400. Because, as noted above, the first image frame 400 is captured shortly after the patient blinks and serves as the basis for determining changes to the tear film surface of the contact lens 406 of the patient's eye 408, the first displacement map 602 is illustrated as a solid map. In other words, because the reflection pattern 402 in the first image frame 400 is taken shortly after the patient blinks, there may be no visible changes to the tear film surface of the contact lens 406 and, as such, locations of the edges of the placido rings 404 have not moved.

FIG. 6B illustrates a second displacement map 604 corresponding to the reflection pattern 502 of the placido rings 404 in the second image frame 500. As noted above, because the second image frame 500 is captured at a second time after the first image frame 400 is captured, the reflection pattern in the second image frame 500 includes the first change 506 and the second change 508 of the tear film of the contact lens 406. The imaging apparatus may determine the first change 506 and the second change 508 based on a comparison of the locations of the edges of the placido rings 404 in the second image frame 500 to the locations of the edges of the placido rings 404 in the first image frame.

For example, based on the comparison between the first image frame 400 and the second image frame 500, the imaging apparatus may determine that the locations of the edges of the placido rings 404 occurring in an area corresponding to the first change 506 in the second image frame 500 have been displaced by a certain amount as compared to the locations of the edges of the placido rings 404 occurring in an area corresponding to the first change 506 in the first image frame 400. Similarly, based on the comparison between the first image frame 400 and the second image frame 500, the imaging apparatus may determine that the locations of the edges of the placido rings 404 occurring in an area corresponding to the second change 508 in the second image frame 500 have been displaced by a certain amount as compared to the locations of the edges of the placido rings 404 occurring in an area corresponding to the second change 508 in the first image frame 400.

The imaging apparatus may then map the displacements of the edges of the placido rings 404 within the second displacement map 604. For example, in FIG. 6B, the displacements of the edges of the placido rings 404 in the second displacement map 604 may be represented by the different densities of stippling. For example, as can be seen, because the locations of the edges of the placido rings 404 in the locations of the first change 506 and the second change 508 of the second image frame 500 have been displaced by a certain amount relative to the first image frame, the stippling shown in the second displacement map 604 of FIG. 6B is more dense in the locations of the first change 506 and the second change 508 as compared to other locations in the second image frame 500 where locations of edges of the placido rings 404 have not changed relative to the first image frame 400. As such, this denser stippling in the second displacement map 604 indicates the locations of the first change 506 and the second change 508 relative to the contact lens 406 worn on the patient's eye 408.

As noted above, the plurality of displacement maps generated at block 340 of FIG. 3 may indicate changes (e.g., breakups) to the tear film surface of the contact lens 406 during the period of time over which the video data and plurality of image frames are captured. To quantify the changes to the tear film surface of the contact lens 406, the imaging apparatus is configured to determine and output, at block 350 of FIG. 3, one or more metrics. In some embodiments, outputting the one or more metrics may include, for example, displaying the one or more metrics on the monitor 216 illustrated in FIG. 2, storing the one or more metrics in memory of the computer 214 or memory external to the computer 214 (e.g., an external server, a flash drive, etc.), printing the one or more metrics using a printer, and the like. In some embodiments, rather than the imaging apparatus determining and outputting the one or more metrics, the imaging apparatus may send data, such as the video data and/or plurality of displacement maps to an external entity or server. In response, the imaging apparatus may receive the one or more metrics from the external entity or server and may output the one or more metrics at block 350 of FIG. 3.

In some embodiments, the one or more metrics comprise one or more tear film breakup times associated with the tear film surface of the contact lens. For example, in some embodiments, the one or more tear film breakup times comprise a first tear film breakup time associated with a center portion of the contact lens (e.g., a tear film breakup time associated with the second change 508) and/or a second a tear film breakup time associated with a peripheral portion of the contact lens (e.g., a tear film breakup time associated with the first change 506). In some embodiments, the imaging apparatus may determine the one or more tear film breakup times based on a displacement of an edge associated with the one or more placido rings from at least a first image frame (e.g., the first image frame 400) to a second image frame (e.g., the second image frame 500) and indicated by the plurality of maps (e.g., the first displacement may 602 and the second displacement map 604) of the tear film surface.

As noted above, the video data and plurality of image frames of the one or more placido rings projected on the tear-film surface of the contact lens are captured over a period of time and, as a result, changes to the tear film surface of the contact lens may continue to change over this period of time. For example, during the period of time over which the video data and plurality of image frames are captured, the first change 506 and second change 508 of the tear film surface of the contact lens 406 may grow in size and, as a result, change in location. Accordingly, to better quantify the changes to the tear film surface (e.g., as breakups grow and move), the one or more metrics may include one or more metrics related to a velocity, acceleration, or magnitude of breakups of the tear film surface.

More specifically, in some embodiments, the one or more metrics determined/output by the imaging apparatus at block 350 of FIG. 3 may comprise one or more tear film breakup velocity metrics associated with the tear film surface of the contact lens. For example, in some embodiments, the one or more tear film breakup velocity metrics may include a first tear film breakup velocity metric associated with a breakup of the tear film surface of the contact lens near a center portion of the contact lens (e.g., a first tear film breakup velocity associated with the second change 508) and/or a second tear film breakup velocity metric associated with a breakup of the tear film surface of the contact lens near a peripheral portion of the contact lens (e.g., a second tear film breakup velocity associated with the first change 506). The tear film breakup velocity metrics may indicate how fast a breakup in the tear film is moving and may be determined in the units of millimeters per milliseconds or other units. In some embodiments, the imaging apparatus may determine the one or more tear film breakup velocity metrics based on a rate of change of displacement of an edge associated with the one or more placido rings from at least a first image frame (e.g., the first image frame 400) to a second image frame (e.g., the second image frame 500) and indicated by the plurality of maps (e.g., the first displacement may 602 and the second displacement map 604) of the tear film surface.

In some embodiments, the one or more metrics determined/output by the imaging apparatus at block 350 of FIG. 3 may comprise one or more tear film breakup acceleration metrics associated with the tear film surface of the contact lens. For example, in some embodiments, the one or more tear film breakup acceleration metrics may include a first tear film breakup acceleration metric associated with a breakup of the tear film surface of the contact lens near a center portion of the contact lens (e.g., a first tear film breakup acceleration associated with the second change 508) and/or a second tear film breakup acceleration metric associated with a breakup of the tear film surface of the contact lens near a peripheral portion of the contact lens (e.g., a second tear film breakup acceleration associated with the first change 506). The tear film breakup acceleration metrics may indicate a rate of change of velocity associated with a breakup in the tear film and may be determined in the units of millimeters per milliseconds squared ($mm/ms^2$) or other equivalent units. In some embodiments, the imaging apparatus may determine the one or more tear film breakup acceleration metrics based on a rate of change of velocity of an edge associated with the one or more placido rings through a plurality of image frames, such as at least a first image frame (e.g., the first image frame 400) to a second image frame (e.g., the second image frame 500), as indicated by the plurality of maps (e.g., the first displacement map 602 and the second displacement map 604) of the tear film surface.

In some embodiments, the one or more metrics determined/output by the imaging apparatus at block 350 of FIG. 3 may include one or more tear film breakup magnitude metrics associated with the tear film surface of the contact lens. For example, in some embodiments, the one or more tear film breakup velocity metrics may include first tear film breakup magnitude metric associated with a breakup of the tear film surface of the contact lens near a center portion of the contact lens (e.g., a first tear film breakup magnitude metric associated with the second change 508) and/or a second tear film breakup magnitude metric associated with a breakup of the tear film surface of the contact lens near a peripheral portion of the contact lens (e.g., a second tear film breakup magnitude metric associated with the first change 506). The first and second magnitude metrics may indicate how big (e.g., in terms of area) the breakups associated with the center and peripheral portions of the contact lens are (e.g., how big the first change 506 and the second change 508 are). In some cases, the magnitude metrics may be determined in different units of area, such a millimeters squared, micrometers squared, pixels squared, and the like. In some embodiments, the imaging apparatus may determine the one or more tear film breakup magnitude metrics based on an area of displacement of an edge associated with the one or more placido rings from at least a first image frame (e.g., the first image frame 400) to a second image frame (e.g., the second image frame 500) and indicated by the plurality of maps (e.g., the first displacement may 602 and the second displacement map 604) of the tear film surface.

In some case, to better quantitatively assess tear-film dynamics of contact lenses, the process 300 may be performed under different testing conditions. For example, in some embodiments, the imaging apparatus may be configured to capture the video data of the one or more placido rings projected on the tear film surface of the contact lens at block 320 of FIG. 3 for at least one of different humidity levels, different eye drop types, different blinking conditions, or different contact lens wear times. Further, further, in some cases, the process 300 may be performed for different contact lenses under similar testing conditions, such as similar humidity levels, similar blinking conditions, and similar eye drop types. Performing the process 300 under similar testing conditions for different contact lens may allow these different contact lens types to be compared against each other.

In some embodiments, the process 300 may also include, outputting one or more recommendations regarding the contact lens based on the one or more metrics that quantify the changes to the tear film surface of the contact lens over the period of time. For example, in some embodiments, the one or more recommendations regarding the contact lens comprise at least one of a recommendation to manufacture the contact lens with certain manufacturing materials, a recommendation to use certain eye drops with the contact lens, a recommendation to change a shape of the contact lens, or a recommendation to use the contact lens with eyes with a particular corneal shape.

Figure 7:
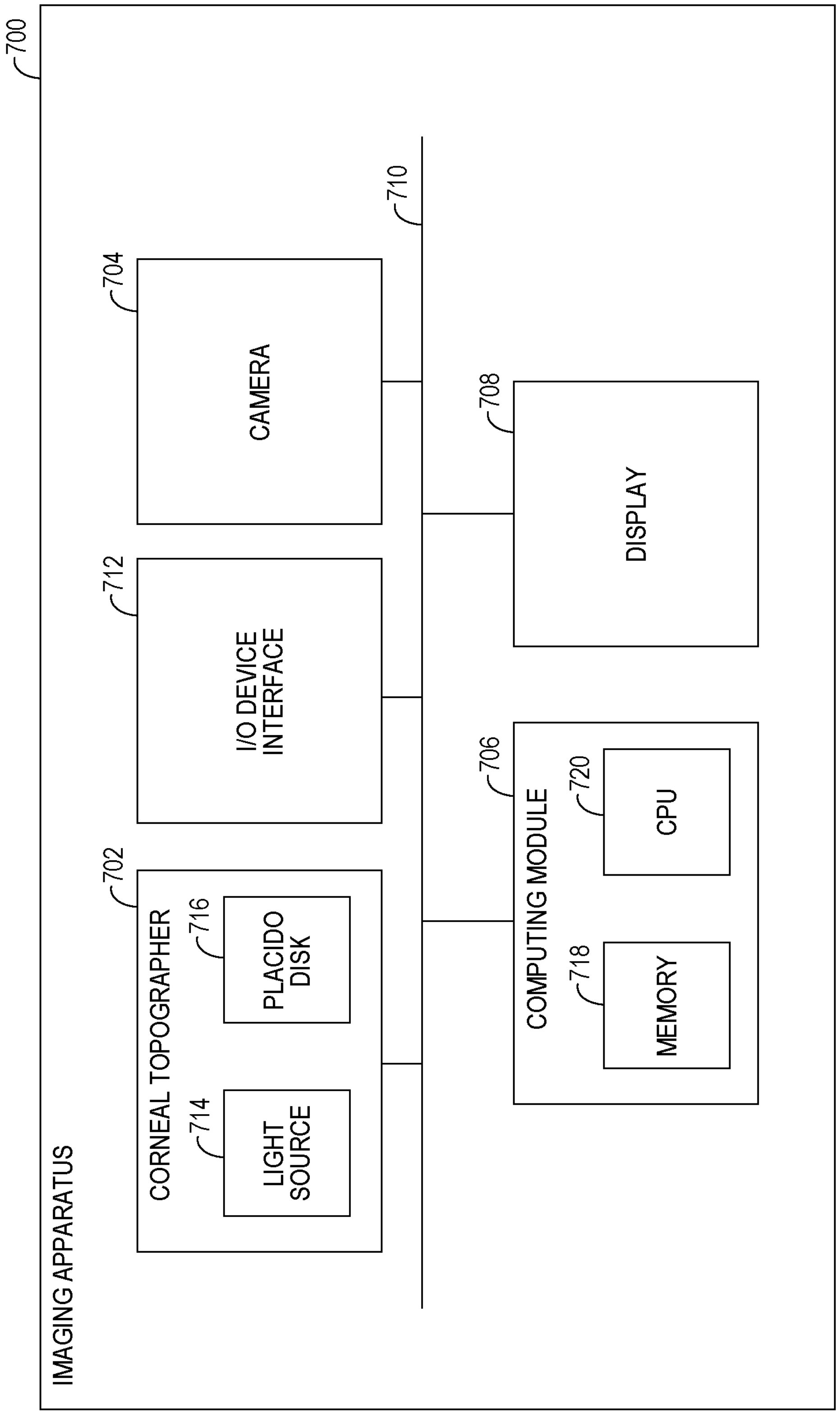
FIG. 7 illustrates an exemplary diagram showing how various components of the imaging apparatus, utilized in conjunction with certain embodiments described herein, communicate and operate together.

FIG. 7 illustrates an exemplary diagram showing how various components of an imaging apparatus 700 communicate and operate together. In some embodiments, the imaging apparatus 700 may be the imaging apparatus described with respect to FIG. 3 that performs the process 300 for tear film analysis of a contact lens worn on an eye.

As shown, the imaging apparatus 700 includes, without limitation, a corneal topographer 702, a camera 704, a computing module 706, a display 708, an interconnect 710, and at least one I/O device interface 712, which may allow for the connection of various I/O devices (e.g., keyboards, displays, mouse devices, pen input, etc.) to imaging apparatus 700.

Further, as shown, the a corneal topographer 702, which may be an example of the corneal topographer 202 in FIG. 2, may include at least a light source 714 and a placido disk 716. The placido disk 716 may translucent and include a known pattern of placido rings or other grid pattern (e.g., a matrix of dots). The light source 714 may be configured to emit light through the placido disk 716 and project an image of one or more placido rings on a tear film surface of a contact lens worn on an eye of a patient.

The camera 704 may include a digital charged-coupled device (CCD) camera capable of converting light signals into digital electric signals. In some embodiments, the camera 704 may be configured to capture video data of the one or more placido rings projected on the tear film surface of the contact lens over a period of time. In some embodiments, the video data captured by the camera 704 may include a plurality of image frames and each image frame of the plurality of image frames includes a reflection pattern of the one or more placido rings at a particular point in time at which that image frame is captured. In some embodiments, the video data captured by the camera 704 may be sent to the computing module 706 of the imaging apparatus 700 for storage and processing.

As shown, the computing module 706 includes at least a memory 718 and a central processing unit (CPU) 720. CPU 720 may retrieve and execute programming instructions stored in the memory 718. Similarly, CPU 720 may retrieve and store application data residing in memory 718. Interconnect 710 transmits programming instructions and application data, among CPU 720, I/O device interface 712, display 708, memory 718, corneal topographer 702, camera 704, etc. CPU 720 can represent a single CPU, multiple CPUs, a single CPU having multiple processing cores, and the like. Additionally, in certain embodiments, memory 718 may include volatile memory (e.g., random access memory). Furthermore, in certain embodiments, memory 718 may also include non-volatile memory (e.g., a disk drive). Although shown as a single unit, memory 718 may be a combination of fixed or removable storage devices, such as fixed disc drives, removable memory cards or optical storage, network attached storage (NAS), or a storage area-network (SAN).

As noted above, in some embodiments, the computing module 706 may be configured to receive video data from the camera 704. Thereafter, in some embodiments, the CPU 720 of the computing module 706 may be configured to perform image segmentation on a plurality of the reflection patterns of the plurality of image frames in the video data received from the camera 704. In some embodiments, the CPU 720 may be configured to perform the image segmentation based on an artificial intelligence (AI) model trained to perform image segmentation of images including reflection patterns associated with contact lenses. In some embodiments, the AI model may be stored in the memory 718 of the computing module 706.

Additionally, in some embodiments, the CPU 720 of the computing module 706 may be configured to generate a plurality of maps of the tear film surface of the contact lens based on the image segmentation performed on the plurality of the reflection patterns. In some embodiments, the plurality of maps may indicate changes to the tear film surface of the contact lens during the period of time and may be stored in the memory 718.

Further, in some embodiments, the CPU 720 may be configured to determine and output, based on the plurality of maps, one or more metrics quantifying the changes to the tear film surface of the contact lens over the period of time. In some embodiments, outputting the one or more metrics may include storing the one or more metrics in the memory 718 and/or displaying the one or more metrics using the display 708. Additionally, in some embodiments, the CPU 720, may also be configured to determine and output one or more recommendations regarding the contact lens based on the one or more metrics that quantify the changes to the tear film surface of the contact lens over the period of time. In some embodiments, outputting the one or more recommendations may include storing the one or more recommendations in the memory 718 and/or displaying the one or more recommendations using the display 708.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. An imaging apparatus for tear film analysis of a contact lens worn on an eye, comprising:

a corneal topographer configured to project an image of one or more predefined shapes onto a tear film surface of the contact lens worn on the eye;

a digital camera configured to capture video data of the one or more predefined shapes projected onto the tear film surface of the contact lens over a period of time, wherein the video data comprises a plurality of image frames and each image frame of the plurality of image frames includes a reflection pattern of the one or more predefined shapes at a particular point in time at which that image frame is captured; and at least one processor, coupled with a memory, configured to cause the imaging apparatus to:

perform image segmentation on the reflection pattern of each of the plurality of image frames to identify edges associated with the one or more predefined shapes;

generate a plurality of maps of the tear film surface of the contact lens based on displacement of the identified edges associated with the one or more predefined shapes from at least a first image frame to a second image frame of the plurality of image frames, the plurality of maps indicating a distortion of at least a portion of the one or more predefined shapes corresponding to changes to the tear film surface of the contact lens during the period of time; and output, based on the plurality of maps, one or more metrics quantifying the changes to the tear film surface of the contact lens over the period of time.

2. The imaging apparatus of claim 1, wherein the at least one processor is configured to cause the imaging apparatus to perform the image segmentation based on an artificial intelligence (AI) model trained to perform image segmentation of images including reflection patterns associated with contact lenses to identify edges associated with the one or more predefined shapes.

3. The imaging apparatus of claim 1, wherein:

the one or more predefined shapes comprise one or more placido rings, and the one or more metrics comprise one or more tear film breakup times associated with the tear film surface of the contact lens.

4. The imaging apparatus of claim 3, wherein the one or more tear film breakup times comprise at least one of:

a first tear film breakup time associated with a center portion of the contact lens, or a second a tear film breakup time associated with a peripheral portion of the contact lens.

5. The imaging apparatus of claim 3, wherein the at least one processor is further configured to cause the imaging apparatus to determine the one or more tear film breakup times based on a displacement of an edge associated with the placido rings from at least a first image frame to a second image frame and indicated by the plurality of maps of the tear film surface.

6. The imaging apparatus of claim 1, wherein:

the one or more predefined shapes comprise one or more placido rings, and the one or more metrics comprise one or more tear film breakup velocity metrics associated with the tear film surface of the contact lens.

7. The imaging apparatus of claim 6, wherein the one or more tear film breakup velocity metrics comprise at least one of:

a first tear film breakup velocity metric associated with a breakup of the tear film surface of the contact lens near a center portion of the contact lens, or a second tear film breakup velocity metric associated with a breakup of the tear film surface of the contact lens near a peripheral portion of the contact lens.

8. The imaging apparatus of claim 6, wherein the at least one processor is further configured to cause the imaging apparatus to determine the one or more tear film breakup velocity metrics based on a rate of change of displacement of an edge associated with the placido rings from at least a first image frame to a second image frame and indicated by the plurality of maps of the tear film surface.

9. The imaging apparatus of claim 1, wherein:

the one or more predefined shapes comprise one or more placido rings, and the one or more metrics comprise one or more tear film breakup magnitude metrics associated with the tear film surface of the contact lens.

10. The imaging apparatus of claim 9, wherein the one or more tear film breakup magnitude metrics comprise at least one of:

a first tear film breakup magnitude metric associated with a breakup of the tear film surface of the contact lens near a center portion of the contact lens, or a second tear film breakup magnitude metric associated with a breakup of the tear film surface of the contact lens near a peripheral portion of the contact lens.

11. The imaging apparatus of claim 9, wherein the at least one processor is further configured to cause the imaging apparatus to determine the one or more tear film breakup magnitude metrics based on an area of displacement of an edge associated with the placido rings from at least a first image frame to a second image frame and indicated by the plurality of maps of the tear film surface.

12. The imaging apparatus of claim 1, wherein the plurality of maps indicates displacement of the identified edges at different portions of the tear film surface of the contact lens.

13. The imaging apparatus of claim 1, wherein the at least one processor is further configured to cause the imaging apparatus to output one or more recommendations regarding the contact lens based on the one or more metrics that quantify the changes to the tear film surface of the contact lens over the period of time, wherein the one or more recommendations regarding the contact lens comprise at least one of:

a recommendation to manufacture the contact lens with certain manufacturing materials, a recommendation to use certain eye drops with the contact lens, a recommendation to change a shape of the contact lens, or a recommendation to use the contact lens with eyes with a particular corneal shape.

14. A method for tear film analysis of a contact lens worn on an eye, comprising:

projecting an image of one or more predefined shapes onto a tear film surface of the contact lens worn on the eye;

capturing video data of the one or more predefined shapes projected onto the tear film surface of the contact lens over a period of time, wherein the video data comprises a plurality of image frames and each image frame of the plurality of image frames includes a reflection pattern of the one or more predefined shapes at a particular point in time at which that image frame is captured;

performing image segmentation on the reflection pattern of each of the plurality of image frames to identify edges associated with the one or more predefined shapes;

generating a plurality of maps of the tear film surface of the contact lens based on displacement of the identified edges associated with the one or more predefined shapes from at least a first image frame to a second image frame of the plurality of image frames, the plurality of maps indicating a distortion of at least a portion of the one or more predefined shapes corresponding to changes to the tear film surface of the contact lens during the period of time; and outputting, based on the plurality of maps, one or more metrics quantifying the changes to the tear film surface of the contact lens over the period of time.

15. The method of claim 14, wherein performing the image segmentation is based on an artificial intelligence (AI) model trained to perform image segmentation of reflection patterns associated with contact lenses to identify edges associated with the one or more predefined shapes.

16. The method of claim 14, wherein:

the one or more predefined shapes comprise one or more placido rings, the one or more metrics comprise one or more tear film breakup times associated with the tear film surface of the contact lens, the one or more tear film breakup times comprise at least one of:

a first tear film breakup time associated with a center portion of the contact lens, or a second tear film breakup time associated with a peripheral portion of the contact lens, and the method further comprises determining the one or more tear film breakup times based on a displacement of an edge associated with the placido rings from at least a first image frame to a second image frame and indicated by the plurality of maps of the tear film surface.

17. The method of claim 14, wherein:

the one or more predefined shapes comprise one or more placido rings, the one or more metrics comprise one or more tear film breakup velocity metrics associated with the tear film surface of the contact lens, the one or more tear film breakup velocity metrics comprise at least one of:

a first tear film breakup velocity metric associated with a breakup of the tear film surface of the contact lens near a center portion of the contact lens, or a second tear film breakup velocity metric associated with a breakup of the tear film surface of the contact lens near a peripheral portion of the contact lens, and the method further comprises determining the one or more tear film breakup velocity metrics based on a rate of change of displacement of an edge associated with the placido rings from at least a first image frame to a second image frame and indicated by the plurality of maps of the tear film surface.

18. The method of claim 14, wherein:

the one or more predefined shapes comprise one or more placido rings, the one or more metrics comprise one or more tear film breakup magnitude metrics associated with the tear film surface of the contact lens, the one or more tear film breakup magnitude metrics comprise at least one of:

a first tear film breakup magnitude metric associated with a breakup of the tear film surface of the contact lens near a center portion of the contact lens, or a second tear film breakup magnitude metric associated with a breakup of the tear film surface of the contact lens near a peripheral portion of the contact lens, and the method further comprises determining the one or more tear film breakup magnitude metrics based on an area of displacement of an edge associated with the placido rings from at least a first image frame to a second image frame and indicated by the plurality of maps of the tear film surface.

19. The method of claim 14, further comprising capturing the video data of the one or more predefined shapes projected onto the tear film surface of the contact lens for at least one of different humidity levels, different eye drop types, or different blinking conditions, different contact lenses, or different contact lens wear times.

20. The method of claim 14, further comprising generating the plurality of maps such that the plurality of maps indicates displacement of the identified edges at different portions of the tear film surface of the contact lens.

* * * * *